United States Patent [19]

Wardle

[11] Patent Number: 5,428,165
[45] Date of Patent: Jun. 27, 1995

[54] PROCESS FOR MAKING 5-INTROBARBITURIC ACID AND SALTS THEREOF

[75] Inventor: Robert W. Wardle, Logan, Utah

[73] Assignee: Thiokol Corporation, Ogden, Utah

[21] Appl. No.: 179,737

[22] Filed: Jan. 10, 1994

Related U.S. Application Data

[63] Continuation-in-part of Ser. No. 178,215, Jan. 6, 1994.

[51] Int. Cl.6 .......................... C07D 239/02
[52] U.S. Cl. ................................ 544/301
[58] Field of Search .......................... 544/301

[56] References Cited

U.S. PATENT DOCUMENTS

| | | | |
|---|---|---|---|
| 2,090,594 | 8/1937 | Jacobson | 260/33 |
| 3,719,604 | 3/1973 | Prior et al. | 252/186 |
| 4,142,029 | 2/1979 | Illy | 521/95 |
| 4,608,102 | 8/1986 | Krampen et al. | 149/92 |
| 4,948,439 | 8/1990 | Poole et al. | 149/46 |
| 5,015,309 | 5/1991 | Wardle et al. | 149/19.1 |
| 5,035,757 | 7/1991 | Poole | 149/46 |
| 5,084,118 | 1/1992 | Poole | 149/22 |
| 5,139,588 | 8/1992 | Poole | 149/61 |
| 5,197,758 | 3/1993 | Lund et al. | 280/741 |

OTHER PUBLICATIONS

D. I. Weisblat & D. A. Lyttle, The Chemistry of Nitroacetic Acid and Its Esters. II. The Synthesis of Ethyl α-Nitro-β-(3-indole)-propionate from Gramine and Ethyl Nitromalonate, J. Am. Chem Soc., 71:2079 (1949).

"Barbituric Acid", J. B. Dickey and A. R. Gray, Organic Syntheses, Collective vol. II, p. 60.

"Nitrobarbituric Acid", W. W. Hartman and O. E. Sheppard, Ogranic Syntheses, Collective vol. II, pp. 440–441. (1943).

"The Diliturates (5–Nitrobarbiturates) of Some Physiologically Important Bases", C. E. Redemann and Carl Niemann, Journal of American Chemical Society, vol. 62, 1940, pp. 590–593.

"New Syntheses of Dilituric Acid", R. Nutiu and I. Sebe, Chemical Abstracts, vol. 75, 1971, p. 460.

"New Syntheses of Dilituric Acid", R. Nutiu and I. Sebe, Rev. Roum. Chim., 1971, vol. 16, pp. 919–923.

"Azione Dell'HCI Gasoso Sull'eters Nitro–Cianacetico In Soluzione Alcoolica", Gazz. Chim. Ital., vol. 42, pp. 223–224.

"The Nitraction Of 4–Methoxy– and 4–Ethoxy Benzophenone", J. Van Alphen, Recviel Trav. Chem. Pay–Bas., vol. 8, pp. 381–382 (1930).

"Contributions a la Connaissance de L'action de L'acide Azotique sur les Corps Organiques", MM. A. P. N. Franchimont and E. A. Klobbie, Recviel Trav. Chem. Pay-Bas., vol. 49, pp. 283–306.

"Darstellug von Barbitursäure und N–Alkyl–barbitursäuren", Heinrich Biltz und Herbert Wittek, Ber. vol. 54, pp. 1035–1058 (1921).

*Primary Examiner*—Cecilia Tsang
*Attorney, Agent, or Firm*—Madson & Metcalf; Ronald L. Lyons

[57] ABSTRACT

A process for preparing salts of 5-nitrobarbituric acid involves allowing an in situ generated a compound represented by formula (I):

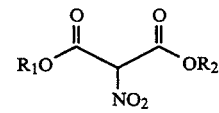

wherein $R_1$ and $R_2$ are the same or different and are, H, $C_1$ to $C_8$ alkyl or substituted $C_1$ to $C_8$ alkyl, aryl or substituted aryl, to condense with urea to obtain a condensation product; and neutralizing the condensation product with at least one organic base and another cation source (MX) at a $pH \geq 7$ and recovering the thus formed salt of 5-nitrobarbituric acid.

18 Claims, No Drawings

PROCESS FOR MAKING 5-INTROBARBITURIC ACID AND SALTS THEREOF

RELATED APPLICATIONS

This application is a continuation in part of copending application No. 08/178,215, filed Jan. 6, 1994 pending titled Gas Generant Composition Containing Non-Metallic Salts of 5-Nitrobarbituric Acid, the complete disclosure of which is incorporated herein by reference.

FIELD OF THE INVENTION

The present invention concerns improved processes for making 5-nitrobarbituric acid and salts thereof.

BACKGROUND OF THE INVENTION

A conventional process for making 5-nitrobarbituric acid, sometimes referred to as dilituric acid, is the direct nitration of barbituric acid. The procedure is described in publications such as, for instance, *Organic Synthesis*, Coll. Vol. II:440–41 and *J. Am. Chem. Soc.* 62:590–3 (1940). In the conventional process barbituric acid is first prepared. One well-known synthesis of barbituric acid starts with the reaction of chloroacetic acid with sodium dicyanamide and esterification with absolute ethanol in the presence of sulfuric acid to form diethyl malonate which is isolated and purified by distillation. The diethyl malonate is subsequently allowed to condense with urea under basic conditions and then acidified to afford barbituric acid. Other conventional processes for preparing barbituric acid include the action of phosphorus oxychloride on malonic acid and urea as described in *Compt. Rend.*, 87:752 (1878), the reaction of ethyl malonate and a sodium derivative of urea obtained from urea and sodium in liquid ammonia as described in U.S. Pat. No. 2,090,594, and a reaction sequence involving dissolving finely cut sodium in absolute alcohol, adding ethyl malonate, adding dry urea in hot absolute ethanol and refluxing before recovering the product as described in *Organic Synthesis*, Coll. Vol. II: 60–61. Other methods for preparing barbituric acid are mentioned in *Organic Synthesis*, Coll. Vol. II: 60–61. The barbituric acid is isolated and then nitrated with fuming or concentrated nitric acid to obtain 5-nitrobarbituric acid.

Another known process for preparing 5-nitrobarbituric acid is the oxidation of violuric acid as described in *Ber.*, 16: 1134 (1883).

Salts of 5-nitrobarbituric acid are obtained by isolating the 5-nitrobarbituric acid and then forming the salt in water.

Although seemingly facile, the conventional processes for making 5-nitrobarbituric acid and its salts are cumbersome and unsuited for large scale production of 5-nitrobarbituric acid and salts thereof. In some conventional processes, five separate direct synthetic operations are carried out, with isolation of intermediate products and, in at least one instance, purification of an isolated intermediate product being required. For instance, the isolation and purification of 5-nitrobarbituric acid can be time consuming and difficult.

It would, therefore, be a significant advance in the art to provide a simpler and more cost-effective process for making 5-nitrobarbituric acid and salts thereof. It would be a further advance in the art to provide a process suitable for the large scale manufacture of 5-nitrobarbituric acid and salts thereof.

Such processes are disclosed and claimed herein.

SUMMARY AND OBJECTS OF THE INVENTION

The processes for producing 5-nitrobarbituric acid of the present invention include in situ preparation of a compound the formula (I)

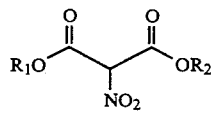

wherein $R_1$ and $R_2$ are the same or different and are H, alkyl or substituted alkyl, aryl, or substituted aryl, and in situ condensation with an effective amount of urea to obtain 5-nitrobarbituric acid. Salts are obtained by treating the reaction product, 5-nitrobarbituric acid, with an effective amount of a compound such as an organic base or another cation source (MX).

The processes according to the present invention are simpler and more cost-effective than conventional processes for making 5-nitrobarbituric acid and its salts. Isolation and purification of reaction intermediates in the synthesis of 5-nitrobarbituric acid and its salts are not required in practicing the present inventions. For instance, according to the present invention isolation of a compound represented by formula (I), barbituric acid, and 5-nitrobarbituric acid is avoided.

DETAILED DESCRIPTION OF THE INVENTION

The present invention provides processes for producing 5-nitrobarbituric acid and its salts.

In one embodiment, a compound having the formula (I)

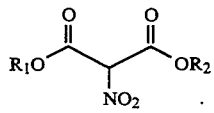

wherein $R_1$ and $R_2$ are the same or different and are H, $C_1$ to $C_8$ alkyl or substituted $C_1$ to $C_8$ alkyl, aryl, or substituted aryl, is condensed with an effective amount of urea to obtain 5-nitrobarbituric acid at a pH which is sufficient to allow the condensation reaction to proceed. $R_1$ and $R_2$ are, independently of one another, H, an alkyl group such as, for instance, methyl, ethyl, n-propyl, i-propyl, n-butyl, i-butyl, t-butyl, or an alkyl substituted with, for instance, methoxy, ethoxy, or halo (such as chloro or bromo), or an aryl group such as, for instance, phenyl or benzyl.

In general, in the aforementioned condensation with urea, the pH is greater than about 7. The pH can be in the range of 10 to 14, except when $R_1$ and $R_2$ are hydrogen at which time the reaction is typically run at a pH less than 7, generally $2 \leq pH \leq 5$, although the precise pH is not critical as long as the condensation reaction proceeds. The reaction rate can, however, be controlled by selecting and maintaining a pH or range of pH.

The compound of formula (I) is prepared in situ. For instance, nitrated diethyl malonate can be obtained by allowing a haloacetic acid, such as chloroacetic acid, bromoacetic acid or a mixture thereof, to react with an effective amount of at least one cyanide source to obtain a salt of cyanoacetic acid at a pH of, for instance, about 10 to about 14, and reacting the cyanoacetic acid salt with an effective amount of nitric acid at a pH less than 7, preferably less than about 3, followed by addition of ann effective amount of ethanol. Preparing nitrated diethyl malonate, a compound according to formula (I), by the direct nitration of cyanoacetic acid is described in, for instance, *Gazzeta Chimica Italiana,* 42:223, the complete disclosure of which is incorporated herein by reference. The nitrations can be conducted at a pH in the range of about 1 to about 5. Other compounds represented by formula (I) can be prepared by replacing ethanol with another alcohol such as, for instance, methanol, propanol, butanol, hexanol, and mixtures thereof. Exemplary cyanide sources include, among others, alkali metal cyanide, such as sodium cyanide and potassium cyanide, alkaline earth metal cyanide, such as calcium cyanide, and $Cu(CN)_2$. Besides nitric acid, other exemplary nitrating reagents include, among others, acetic acid or acetic anhydride with ammonium nitrate, acetic acid or acetic anhydride with one or more metal nitrates of which $Mn(NO_3)_2$, $Cu(NO_3)_2$, $NaNO_3$, $Ca(NO_3)_2$, $Mg(NO_3)_2$, and $Sr(NO_3)_2$ are illustrative. By preference, these nitrating reagents are only used in slight excess because the substrate is facilely nitrated.

As will be apparent, the pH of the in situ reaction mixture is adjusted to a $pH \geq 7$, preferably higher, during, or just before, the condensation with urea.

In another embodiment, the cyanoacetic acid can be nitrated and the cyano group hydrolyzed to form nitromalonic acid (compound (I), wherein $R_1$ and $R_2$ are H). Nitromalonic acid can be directly converted to dilituric acid by adding an effective amount of a dehydrating agent, such as anhydride, and urea to effect the condensation. Exemplary anhydrides include, among others, acetic anhydride, propionic anhydride, butyric anhydride, and benzoic anhydride. Typical reaction conditions are similar to those described in *Chem. Ber.,* 54:1035 (1921) regarding the condensation of malonic acid with urea to form barbituric acid.

In yet another embodiment, a compound of formula (I) is obtained by nitrating a compound of formula (II)

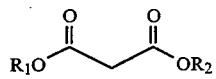

wherein $R_1$ and $R_2$ are as described above, with an effective amount of a nitrating reagent. For example, diethyl malonate can be nitrated to obtain a compound represented by formula (I). Suitable nitrating reagents include, among others, nitric acid, acetic acid or acetic anhydride with ammonium nitrate, acetic acid or acetic anhydride with one or more metal nitrates of which $Mn(NO)_2$, $Cu(NO)_2$, $NaNO_3$, $Ca(NO_3)2$, $Mg(NO_3)_2$, and $Sr(NO_3)_2$ are illustrative. The compound of formula (I) is condensed with an effective amount of urea under conditions described hereinabove. The acid is treated in situ with an effective amount of a compound such as an organic base or another appropriate cation source to form the desired salt.

Other compounds represented by formula (I), such as, for instance, dimethyl nitromalonate, dipropyl nitromalonate, diisopropyl nitromalonate, dibutyl nitromalonate, and dibenzyl nitro malonate, as well as their counterpart compounds of formula (II) can be prepared as above-described.

Salts of 5-nitrobarbituric acid are obtained without need to first isolate barbituric acid or 5-nitrobarbituric acid. According to an embodiment of the present invention, salts of 5-nitrobarbituric acid are obtained by allowing the above-described condensation reaction with urea to proceed and treating the 5-nitrobarbituric acid in situ with an organic base and/or with another cation source (MX). The latter treatment can be conducted either concurrently with the condensation or subsequently to the completion of the condensation reaction. If the latter condensation has been carried out at low pH, the addition of the base would preferably occur after completion of the condensation. If the condensation is conducted at a high pH, the base cane be added concurrently and can be used to control the pH as in the case of, for instance, potassium hydroxide, unless the base will interfere with the condensation as would be expected for many high nitrogen bases such as, for instance, ammonia, hydrazine, and guanidine.

The compound used to form the salt can be an organic base, or other cation source. The appropriate organic base or other cation source useful for neutralizing the urea condensation product can be selected to provide the desired cation. Non-metallic cations can be selected, for instance, from among organic cations and, in principle, cations of non-carbon heterocycles such as borazines. Thus, the cation can be a non-metallic cation of a high nitrogen-content base. Exemplary non-metallic cations include, among others, ammonium, hydrazinium, guanidinium, aminoguanidinium, diaminoguanidinium, triaminoguanidinium, biguanidinium, aminotriazolium, guanizinium, aminotetrazolium, and hydrazino tetrazolium. The other cation source, MX, can be selected from the group consisting of alkali metal salts, alkaline earth metal salts, and salts of transition metals. Exemplary other cation sources MX include potassium hydroxide, potassium chloride, $Zn(NO_3)_2$, NaOH, $SrCl_2$, and the like. By preference the organic base or other cation source (MX) is selected to obtain salts which are readily recovered without extensive work-up. For instance, the sodium salt of 5-nitrobarbituric acid can be formed, but the sodium salt is harder to recover owing to its solubility in water. Organic bases and other cation sources for making salts from 5-nitrobarbituric acid are described in *J. Am. Chem. Soc.,* 62:590 (1940), the complete disclosure of which is incorporated herein by reference.

The 5-nitrobarbituric acid salts can be recovered using techniques known to those skilled in the art. For instance, with those salts having low solubility constants (Ksp) the salt precipitates and can be recovered by filtration or centrifugation. The salts can be further purified, if desired, by re-crystallization.

In general, the reaction conditions selected by a person skilled in the art will be apparent given the disclosure herein. For instance, the displacement of the chloride in chloroacetic acid is typically conducted at reflux in ethanol or DMF. The nitrations are typically carried out at lower temperatures in nitric acid, or in acetic acid/acetic anhydride with nitric acid (acetyl nitrate). The esterifications and condensations are generally carried out at reflux in an appropriate solvent, such as ethanol for the esterification, ethanol for the base catalyzed condensations, acetic acid for the acid catalyzed—anhydride mediated condensations. Base forming reactions, if not conducted in situ, will be conducted at room temperature, although the reactions could, if desired, be conducted at higher or lower temperatures.

Condensation reactions should be conducted with exclusion of moisture by, for instance, a drying tube on the reflux condenser or under dry nitrogen. Urea should be essentially anhydrous. Nitric acid can be the conventional 98%, although lower concentrations such as 70% can be used as well.

The process conditions can be adjusted, if desired, to enhance recovery the salt of 5-nitrobarbituric acid. For instance, the temperature can, of course, be controlled, i.e. raised or lowered or the like, to induce or regulate the rate of precipitation of the desired salt.

Dilituric acid is useful as a reagent for isolating various organic and inorganic bases, for the isolation of magnesium and for the separation of potassium from binary mixtures containing sodium and potassium. Dilituric salts have a variety of uses. For example, the potassium salt of dilituric acid is useful in gas generant compositions as described in U.S. Pat. No. 5,015,309, the complete disclosure of which is incorporated herein by reference.

The invention is described further in the following non-limiting examples.

EXAMPLES

Example 1

Nitration of diethyl malonate in nitric acid (70%) is conducted, followed by base treatment (potassium ethoxide, ethanol) to obtain the desired pH. Urea is added. The condensation mixture is heated to reflux to yield the potassium diliturate salt. The salt is recovered by filtration.

Example 2

Various salts of dilituric acid are prepared.

Nitration of malonic acid with acetyl nitrate in acetic acid/acetic anhydride was conducted to obtain nitromalonic acid. To the nitromalonic acid is added urea to obtain a condensation reaction mixture which is refluxed to form dilituric acid in situ. Various salts are separately prepared from the dilituric acid in situ using as cation sources potassium chloride, ammonia, and guanidinium chloride. The potassium diliturate salt, ammonium diliturate, guanidinium diliturate salts are each recovered and isolated by filtration.

Example 3

Various salts of dilituric acid were prepared in situ.

Nitrocyanoacetic acid is prepared according to *Gazzeta Chimica Italiana*, 42:223 (chloroacetic acid plus NaCN, then nitric acid). To the nitrocyanoacetic acid is added a minimal amount of water to hydrolyze the acid. Heating to reflux yields the nitromalonic acid in situ. Various salts are separately prepared from the dilituric acid in situ using as cation sources potassium chloride, ammonia, and guanidinium chloride. The potassium diliturate salt, ammonium diliturate, guanidinium diliturate salts are each recovered and isolated by filtration.

Example 4

Nitrocyanoacetic acid is prepared as in Example 3 and is esterified by the addition of ethanol and heated to reflux to afford the diethyl nitromalonate in situ. To the diethyl nitromalonate is added potassium ethoxide and ethanol to obtain the desired pH. Urea is added. The condensation mixture is heated to reflux to yield the potassium diliturate salt. The salt is recovered by filtration.

Other or mixed esters of nitromalonate can be obtained by adapting the procedures of this Example.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed:

1. A process for preparing salts of 5-nitrobarbituric acid comprising allowing an in situ generated diethyl nitro malonate to condense with urea to obtain 5-nitrobarbituric acid and neutralizing said acid with a nitrogen containing organic base, ammonium, hydrazinium, alkali metal salts, alkaline earth metal salts, salts of transition metals, or mixtures thereof, and recovering the thus formed salt of 5-nitrobarbituric acid without distillation or isolation of intermediate products during the preparation of the 5-nitrobarbituric acid salts.

2. A process according to claim 1, wherein said organic base comprises a cation selected from the group consisting of guanidinium, aminoguanidinium, diaminoguanidinium, triaminoguanidinium, biguanidinium, aminotriazolium, guanizinium, aminotetrazolium, and hydrazino tetrazolium.

3. A process according to claim 1, wherein the nitrated diethyl malonate is obtained by nitrating diethyl malonate with a nitrating reagent.

4. A process according to claim 3, wherein said nitrating reagent is selected from the group consisting of nitric acid, nitric acid and acetic anhydride, and a mixture of acetic acid and acetic anhydride with ammonium nitrate or at least one metal nitrate.

5. A process according to claim 4, wherein said nitrating reagent is acetic acid or acetic anhydride and a metal nitrate selected from the group consisting of $Mn(NO_3)_2$, $Cu(NO_3)_2$, $NaNO_3$, $Ca(NO_3)_2$, $Mg(NO_3)_2$, and $Sr(NO_3)_2$.

6. A process according to claim 1, wherein the nitrated diethyl malonate is generated in situ by allowing at least one haloacetic acid to react with a cyanide anion source to obtain cyanoacetic acid, and allowing the cyanoacetic acid to react with ethanol in the presence of a nitrating reagent.

7. A process according to claim 6, wherein said haloacetic acid is bromoacetic acid, chloroacetic acid, or a mixture thereof.

8. A process according to claim 6, wherein said cyanide anion source is selected from the group consisting of alkali metal cyanides and alkaline earth metal cyanides.

9. A process according to claim 8, wherein said cyanide anion source is selected from the group consisting of sodium cyanide, potassium cyanide and cupric cyanide.

10. A process according to claim 6, wherein the reaction of cyanoacetic acid with ethanol is conducted at a $pH \leq$ about 2.

11. A process according to claim 6, wherein said nitrating reagent is selected from the group consisting of nitric acid, nitric acid and acetic anhydride, and a mixture of acetic acid and acetic anhydride with ammonium nitrate or at least one metal nitrate.

12. A process according to claim 6, wherein said nitrating reagent is a mixture of acetic acid and acetic anhydride and at least one metal nitrate selected from the group consisting of $Mn(NO_3)_2$, $Cu(NO_3)_2$, $NANO_3$, $Ca(NO_3)_2$, $Mg(NO_3)_2$, and $Sr(NO_3)_2$.

13. A process for preparing salts of 5-nitrobarbituric acid comprising allowing an in situ generated a compound represented by formula (I):

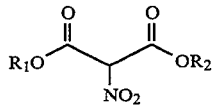

wherein $R_1$ and $R_2$ are the same or different and are, H, $C_1$ to $C_8$ alkyl or substituted $C_1$ to $C_8$ alkyl, aryl or substituted aryl, to condense with urea to obtain a condensation product; and neutralizing the condensation product with at least one member selected from the group consisting of an organic base and another cation source (MX), and recovering the thus formed salt of 5-nitrobarbituric acid without distillation or isolation of intermediate products during the preparation of the 5-nitrobarbituric acid salts.

14. A process for preparing a salt of 5-nitrobarbituric acid comprising adding a dehydrating reagent to nitromalonic acid and urea, and neutralizing the reaction product thereof to obtain a salt of 5-nitrobarbituric acid without distillation or isolation of intermediate products during the preparation of the 5-nitrobarbituric acid salts.

15. A process according to claim 14, wherein said dehydrating reagent is an organic anhydride.

16. A process according to claim 15, wherein said dehydrating reagent is selected from the group consisting of acetic anhydride, propionic anhydride, butyric anhydride, and benzoic anhydride.

17. A process according to claim 14, wherein said neutralization is carried out with a reagent having a cation selected from the group consisting of ammonium and hydrazinium, guanidinium, aminoguanidinium, diaminoguanidinium, triaminoguanidinium, biguanidinium, aminotriazolium, guanizinium, aminotetrazolium, and hydrazino tetrazolium.

18. A process for preparing 5-nitrobarbituric acid comprising generating in situ diethyl nitromalonate and condensing the diethyl nitromalonate with urea and recovering the thus formed 5-nitrobarbituric acid.

* * * * *